United States Patent [19]

Shoup et al.

[11] Patent Number: 5,591,129
[45] Date of Patent: Jan. 7, 1997

[54] PERFUSION BALLOON ANGIOPLASTY CATHETER

[75] Inventors: Michael J. Shoup, Maple Grove; James E. Cox, Plymouth; Paul J. Fordenbacher, Minneapolis; Gregory A. Boldenow, Plymouth, all of Minn.

[73] Assignee: SciMed Life Systems, Inc., Maple Grove, Minn.

[21] Appl. No.: 441,618

[22] Filed: May 15, 1995

Related U.S. Application Data

[63] Continuation-in-part of Ser. No. 204,733, Mar. 2, 1994, abandoned.

[51] Int. Cl.[6] ........................................ A61M 29/00
[52] U.S. Cl. ........................ 604/96; 604/102; 606/194; 606/192
[58] Field of Search ............... 604/96–103, 280–281; 606/191–192, 193

[56] References Cited

U.S. PATENT DOCUMENTS

| | | |
|---|---|---|
| 3,585,983 | 6/1971 | Kastrowitz et al. . |
| 3,834,394 | 9/1974 | Hunter et al. . |
| 4,276,874 | 7/1981 | Wolvek et al. . |
| 4,362,150 | 12/1982 | Lombardi, Jr. et al. . |
| 4,402,307 | 9/1983 | Hanson et al. . |
| 4,444,186 | 4/1984 | Wolvek et al. . |
| 4,581,017 | 4/1986 | Sahota . |
| 4,646,719 | 3/1987 | Neuman et al. . |
| 4,689,041 | 8/1987 | Corday et al. . |
| 4,771,777 | 9/1988 | Horzewski et al. . |
| 4,790,315 | 12/1988 | Mueller, Jr. et al. . |
| 4,877,031 | 10/1989 | Conway et al. . |
| 4,892,519 | 1/1990 | Songer et al. . |
| 4,921,483 | 5/1990 | Wijay et al. . |
| 4,944,745 | 7/1990 | Sogard et al. . |
| 5,000,734 | 3/1991 | Boussignac et al. . |
| 5,046,503 | 9/1991 | Schneiderman . |
| 5,085,635 | 2/1992 | Cragg . |
| 5,087,247 | 2/1992 | Horn et al. . |
| 5,090,958 | 2/1992 | Sahota . |
| 5,158,540 | 10/1992 | Wijay et al. . |
| 5,160,321 | 11/1992 | Sahota . |
| 5,195,971 | 3/1993 | Sirhan . |
| 5,201,723 | 4/1993 | Quinn . |
| 5,279,562 | 1/1994 | Sirhan et al. . |
| 5,295,962 | 3/1994 | Crocker et al. . |
| 5,300,085 | 4/1994 | Yock . |
| 5,334,154 | 8/1994 | Samson et al. . |
| 5,370,617 | 12/1994 | Sahota . |
| 5,378,237 | 1/1995 | Boussignac et al. . |
| 5,383,890 | 1/1995 | Miraki et al. . |
| 5,415,636 | 5/1995 | Forman . |
| 5,421,826 | 6/1995 | Crocker et al. . |
| 5,425,714 | 6/1995 | Johnson et al. . |

FOREIGN PATENT DOCUMENTS

| | | |
|---|---|---|
| 0246998A2 | 11/1987 | European Pat. Off. . |
| 0353889A1 | 2/1990 | European Pat. Off. . |
| 0441384A2 | 8/1991 | European Pat. Off. . |
| 0517654A2 | 12/1992 | European Pat. Off. . |
| 0629417A2 | 12/1994 | European Pat. Off. . |
| WO92/20398 | 11/1992 | WIPO . |

*Primary Examiner*—John D. Yasko
*Assistant Examiner*—Perry E. Van Over
*Attorney, Agent, or Firm*— Nawrocki, Rooney & Sivertson, P.A.

[57] ABSTRACT

A balloon angioplasty catheter having a balloon head assembly carried at the distal end of an elongated catheter body. The balloon head assembly includes an inflatable balloon envelope and a perfusion lumen extending through the balloon envelope to provide a blood flow passage during inflation of the balloon envelope. In a preferred embodiment, the perfusion lumen is formed by a helical member having spaced coils encapsulated with a flexible material. A discharge lumen is formed by a projecting tip, the tip being integrally formed with the balloon envelope. Discharge orifices are provided through the tip sidewall. In a preferred embodiment, the side discharge orifices are elongated in the general direction of perfusion flow through the balloon head. The invention also encompasses means for facilitating discharge of perfused blood through the discharge orifices. This is accomplished by valving perfusate flow through the discharge lumen.

33 Claims, 5 Drawing Sheets

PERFUSION BALLOON ANGIOPLASTY CATHETER

CROSS REFERENCE TO RELATED APPLICATIONS

This application is a continuation-in-part of application Ser. No. 08/204,733 filed on Mar. 2, 1994, now abandoned.

BACKGROUND OF THE INVENTION

The present invention relates to angioplasty and, in particular, to perfusion balloon angioplasty catheters.

Balloon catheters are widely used in a variety of intravascular applications. In particular, angioplasty has gained wide acceptance as an efficient and effective treatment for particular vascular conditions. For example, angioplasty is widely used to treat stenoses in coronary arteries, although its application to stenoses in other parts of the vascular system is also known.

The most common form of angioplasty is percutaneous translumenal coronary angioplasty (PTCA) which utilizes a dilatation catheter having an inflatable balloon at its distal end. The catheter is guided through the vascular system, using fluoroscopy, until the balloon is positioned across the stenosis. The balloon is then inflated such that the balloon engages the stenosis to reestablish acceptable blood flow through the artery.

An initial concern with PTCA was the temporary blockage of blood flow during balloon inflation. With increasing clinical experience, this concern declined. The vast majority of patients tolerate 30–60 second dilatations quite well. Concurrently, cardiologists discovered that prolonged dilatations can assist with some developments occasionally encountered with angioplasty. For example, prolonged dilatations of several minutes may be employed on the occurrence of dissections, intimal flaps, acute thrombolysis and vessel spasms. The profound ischemia of long dilatation is outweighed by the potential prevention of emergency coronary bypass surgery.

A variety of techniques have been proposed to facilitate prolonged dilatations. These include the use of pharmacologic agents to improve myocardial tolerance of ischemia, synchronized retroperfusion, mechanical pump distal perfusion and auto or passive perfusion.

The use of pharmacologic agents treats the symptoms of ischemia without addressing the cause. As a result, this approach is inherently limited.

Synchronized retroperfusion involves pumping blood during diastole into the coronary sinus and then subselectively into the regional coronary veins which drain the jeopardized myocardium. While this approach potentially offers nearly complete myocardial perfusion, it is complicated and cumbersome. Mechanical pump distal perfusion involves pumping blood (or other perfusate) through a lumen of the PTCA catheter. As the name implies, this requires some form of mechanical pump which complicates the angioplasty equipment and procedure.

Auto or passive perfusion has found increasing interest both for prolonged dilatations as well as shorter dilatations having a duration on the order of non-perfusion dilatations. Typically, in passive perfusion, the balloon catheter acts as temporary stent. That is, a perfusion lumen is employed to provide a blood flow passage during balloon inflation. Typically, the perfusion lumen extends through the balloon envelope having an inlet proximal to the balloon envelope and a discharge distal to the balloon envelope. Proposed inlet configurations have included side openings in the catheter as well as a beveled opening to the blood flow channel. Proposed discharge configurations have included a main axial orifice and side openings. Clearly, the inlet and outlet have a direct effect on blood flow capacity. Further, pressure within the balloon envelope during balloon inflation has a tendency to compress a perfusion lumen within the envelope thereby potentially constricting the blood flow passage. On the other hand, countering this tendency by stiffening the perfusion lumen walls can seriously impact trackability of the catheter itself. The attachment of a projecting distal tip to provide side wall discharge can affect trackability as a result in changes of stiffness from material changes and/or the attachment itself.

As discussed above, various proposed discharge configurations have included a main axial orifice and side openings. For a number of reasons, including trackability, it is desirable to be able to control relative egress flow through the main axial orifice and the side openings. Such control can increasingly be a factor when perfusion flow is maximized, for example, where the guide wire along which the catheter is inserted is withdrawn after catheter insertion in order to increase the cross-sectional flow area through the perfusion lumen of the catheter which passes through the balloon envelope.

It is to these dictates of the prior art that the present invention is directed. It is a balloon angioplasty catheter which serves to obviate many of the shortcomings of prior art structures.

SUMMARY OF THE INVENTION

The present invention provides a perfusion balloon catheter particularly adapted to angioplasty of the type having a balloon assembly carried at the distal end of an elongated catheter body. The balloon assembly includes an inflatable balloon envelope and a perfusion lumen extending through the balloon envelope to provide a blood flow passage during inflation of the balloon envelope. In a preferred embodiment, the perfusion lumen is formed of an encapsulating flexible material supported against collapse during balloon inflation by a helical member having spaced coils. The pitch of the spaced coils may be selected to avoid coil-to-coil contact during traverse of a body vessel, as during advance of the catheter through the vascular system during delivery of the catheter to a desired site within the vessel. Blood flow through the perfusion lumen is facilitated in accordance with another aspect of the present invention through side opening configurations which facilitate discharge during perfusion. In a preferred embodiment, the discharge is through generally oval orifices. The orifices are located in a distally projecting tip, the tip being in fluid communication with the perfusion lumen. In a preferred embodiment, the major dimension of the oval orifices is generally aligned with the direction of projection of the projecting tip.

To negate the effect on trackability of stiffness transitions within the balloon head assembly, the present invention provides an integral projecting tip. That is, the balloon envelope and projecting tip of the balloon head assembly are integrally formed. In a preferred embodiment, a plurality of discharge orifices extend through the projecting tip side wall.

In some embodiments, various means can be provided for facilitating preferred discharge through the side opening orifices. Various embodiments of the invention provide different means for accomplishing this. For example, in one embodiment, a gate normally biased to a closed position, is provided at a distal end of the discharge lumen. During catheter installation, the guide wire and an axially displaceable guide wire tube disposed radially intermediate the guide wire and an axially fixed guide wire tube, pass through the gate. After installation is completed, the guide wire and axially displaceable tube can be withdrawn to increase perfusion flow through the perfusion lumen. Upon withdrawal of the guide wire and displaceable tube, the gate, being biased to the closed position, will close in order to direct egress flow through the side orifices.

In other embodiments various other valving/metering structures are employed. In a number of embodiments of the invention, a valve member is carried by the axially displaceable guide wire tube so that, as that tube is moved axially through the discharge lumen, the location of the valve member relative to the discharge lumen distal end main axial orifice can be varied in order to control egress flow. When the valve member is fully closed, all flow will be directed through the side orifices. When the valve member is opened, egress flow will be divided between the side orifices and the main axial orifice.

The present invention is thus an improved balloon angioplasty catheter. More specific features and advantages obtained in view of those features will become apparent with reference to the DETAILED DESCRIPTION OF THE INVENTION, accompanying drawing figures, and appended claims.

BRIEF DESCRIPTION OF THE DRAWINGS

FIG. 11 is a greatly enlarged fragmentary perspective detail thereof showing the distal end of the catheter balloon tip having the guide wire protruding through;

DETAILED DESCRIPTION OF THE INVENTION

Figure 1:
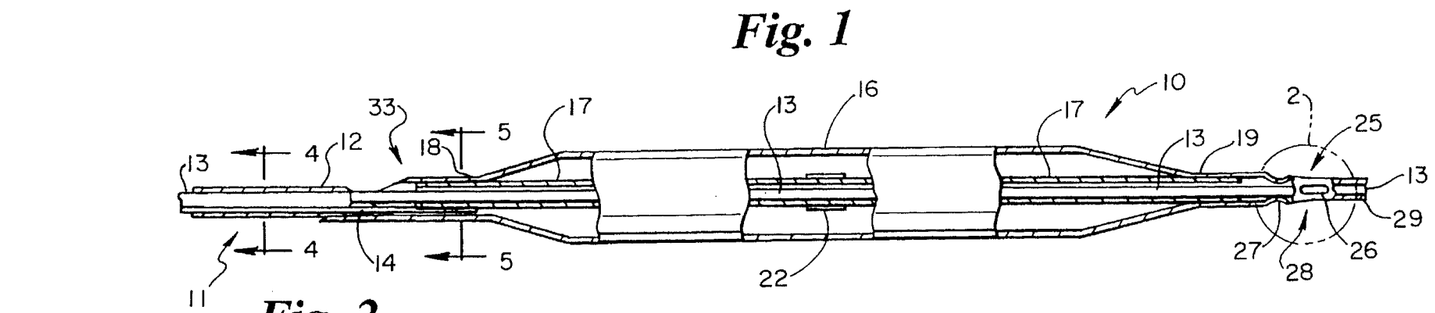
FIG. 1 is a partial cut-away including a balloon head assembly in accordance with the present invention.

FIG. 1 is a partial cut-away of a preferred embodiment of the present invention including a balloon head assembly generally designated at 10, the balloon head 10 being carried at the distal end 11 of an elongated catheter body (partially shown). The embodiment illustrated in FIG. 1 is an over-the-wire angioplasty balloon catheter. The distal terminus 11 of the catheter body includes an outer tubular member 12 surrounding an inner tubular guide wire lumen 13. The space between the outer surface of the guide wire lumen 13 and the inner surface of tubular member 12 provides a passage (an inflation lumen) for inflation of the balloon of balloon assembly 10, in known manner. In the illustrated embodiment, the tubular members 12 and 13 may be formed of polyethylene, for example, while those portions of the catheter body which are not illustrated may be of any conventional design, including a manifold. Fluid communication between the inflation lumen formed by the members 12 and 13 and the interior of the balloon of balloon assembly 10 is via a molded member 14 described more fully below. Molded member 14 may be extruded using polypropylene or polyethylene, for example, or otherwise molded of any suitable material.

Figure 3:
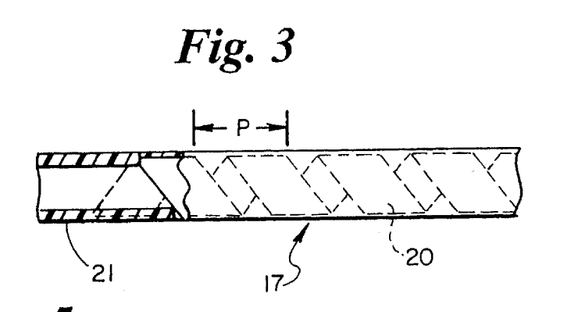
FIG. 3 is a partial cutaway of an enlarged view of a portion of a perfusion lumen in accordance with the present invention.

Balloon assembly 10 includes a balloon envelope 16 which may be formed of a polyethylene/EVA blend, for example. A perfusion lumen 17 extends through the interior of the balloon envelope 16 from a proximal balloon waist 18 to a distal balloon waist 19. The perfusion lumen 17 is partially illustrated in FIG. 3 and is formed of a helical member 20 having spaced coils, the coils being encapsulated within and supporting a flexible material 21 such as urethane. In FIG. 3, the flexible material 21 is partially cut away with the member 20 being shown in phantom where it is encapsulated. The interior of the lumen 17 provides a blood flow passage through the interior of the balloon envelope—from proximal waist 18 to distal waist 19. The coil member 20 supports the lumen against collapse during inflation of the balloon envelop while the spacing of the coils is selected to avoid coil-to-coil contact during traverse of a body vessel. That is, particularly during advance of the catheter over a positioned guide wire, trackability of the catheter assembly is particularly important. The spacing of the coils (their "pitch" represented at "p" in FIG. 3) allows the inflation lumen 17 to flex through bends in the vessel being traversed due to the flexibility of the encapsulating material 21 while supporting that material against collapse during balloon inflation. Determination of coil pitch is within the skill of one ordinarily skilled in the art being dependent, to some extent, on the intended placement site of the balloon along the vessel (and the characteristics of the vessel to be traversed) and the support requirements of the encapsulating material 21. In a preferred embodiment, the helical member 20 is a ribbon of a suitable metal, surgical grade stainless steel, for example, having a thickness of 0.0015", a width of 0.006" and a pitch of 0.008" to 0.010". The helical member 20 may be radiopaque or alternatively, a marker band 22 may be provided, in known manner. The use of an encapsulated coil provides a thinner sidewall than would be the case with a solid wall tube layered with a coil which, in turn, allows a smaller balloon head profile.

Figure 2:
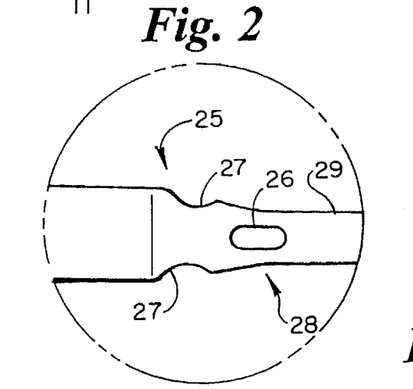
FIG. 2 is an enlarged view of the indicated portion of FIG. 1.

A balloon assembly tip 25 extends distally from the balloon envelope and the distal end of perfusion lumen 17 and defines a discharge lumen therein. The projecting tip 25 is provided with a plurality of discharge orifices 26 and 27 (see FIG. 2) through its side wall. In a preferred embodiment, a first "stage" of three orifices 27 (two being visible in FIG. 2) are positioned equidistantly around the side wall of projecting tip 25 with a second "stage" of orifices 26 being positioned distally from the first stage formed by orifices 27. In the illustrated embodiment, there are three second stage orifices 26 (one being visible in FIG. 2) positioned equidistantly around the tip 25, each being positioned angularly intermediate the orifices 27 of the first stage. In the illustrated and described embodiment, the orifices of each stage are positioned around the tip 120° from the other orifices of their stage, with the orifices of one stage being offset by 60° from the orifices of the other stage.

To facilitate the discharge of flow through the perfusion lumen 17, the side, or side wall, orifices 26 and 27 may be elongated in the direction of extension of the projecting tip 25 and its interior discharge lumen. In the illustrated embodiment, this direction corresponds generally to the flow direction through the perfusion lumen 17. In a preferred embodiment, the orifices 26 and 27 are oval and have an aspect ratio of 1.5 to 1. To further facilitate discharge, the elongated tip 25 is provided with a portion 28 which converges distally, the orifices 26 and 27 passing through the side wall of the converging tip portion 28. The use of elongated orifices through the side wall of a converging tip has been found to significantly increase the flow through the perfusion lumen 17. The terminus 29 of the projecting tip 25 is generally cylindrical.

As described above, the catheter body includes a guide wire lumen 13. The guide wire lumen 13 extends from the catheter body and through the balloon assembly, including the balloon envelope, to terminate within the generally cylindrical portion 29 of projecting tip 25. The guide wire lumen 13 may be stepped down or otherwise decreased in size to facilitate reduction in the profile of the balloon assembly 10, in known manner. The guide wire lumen 13 extends through the perfusion lumen 17 and is bonded, in known manner, within the terminus 29 of projecting tip 25. The interior of projecting tip 25 forms a discharge lumen in fluid communication with the distal end of the perfusion lumen 17 (generally at waist 19) while the bonding of the guide wire lumen 13 at distal tip 29 prevents axial discharge of flow passing through the perfusion lumen 17.

Figure 6:
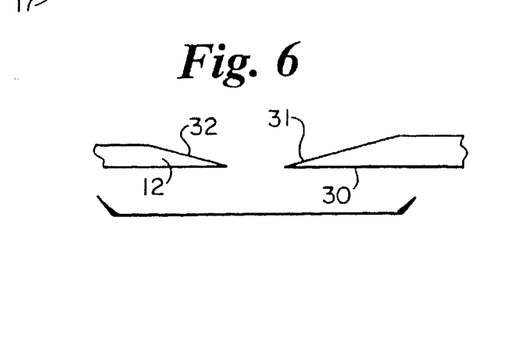
FIG. 6 is an exploded view illustrating the manner of connection of the balloon head assembly to the distal end of the catheter body of the embodiment of FIG. 1.

Balloon waist 18 is generally cylindrical. Balloon assembly 10 further includes a generally cylindrical proximal extension from waist 18 indicated generally at 30. Extension 30 is skived (see FIG. 6) as indicated at 31. Similarly, tubular member 12 is generally cylindrical and is skived as indicated at 32. Extension 30 is larger than tubular member 12 such that member 12 may be positioned within, and bonded to the skived portion of projection 30, so as to provide a blood flow inlet indicated generally at 33 in FIG. 1. Blood flowing through the inlet passes through the extension 30 to the proximal terminus of perfusion lumen 17 (generally at waist 18). Blood passing through perfusion lumen 17 enters the discharge lumen of projection 25 to be discharged through the orifices 26 and 27.

Figure 4:
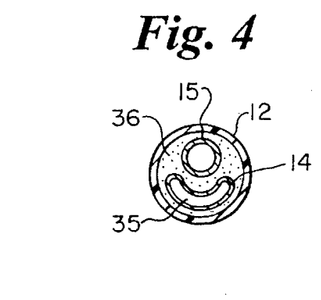
FIG. 4 is a cross section taken along the line 4—4 in FIG. 1.
Figure 5:
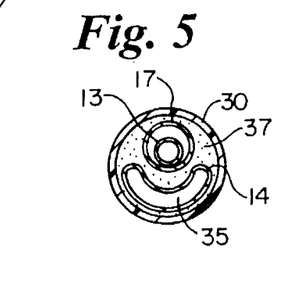
FIG. 5 is a cross section taken along the line 5—5 in FIG. 1.

As described above, molded member 14 extends from the inflation lumen between guide wire lumen 13 and tubular member 12 to the interior of the balloon envelope 16. Member 14 has a divided interior flow lumen or passage for inflation fluid (see FIGS. 4 and 5) the division in the flow lumen of member 14 resulting from the provision of a web 35 which acts to prevent the expansion of the member 14. As illustrated in FIG. 4, the member 14 and guide wire lumen 13 are bonded in a matrix of bonding material 36 at the terminus of the elongated catheter body 11, the bonding material 36 sealing the inflation lumen between the guide wire lumen 13 and sheath 12 of the catheter body. Similarly, the interior of the extension 30 opens to the interior of the flow lumen 17 (the guide wire lumen 13 being positioned within the perfusion lumen 17) with the member 14 extending beyond waist 18 into the interior of the balloon envelope. At the region of the waist 18, a matrix of bonding material 37 seals the interior of the balloon envelope 16 (see FIG. 5).

Figure 7:
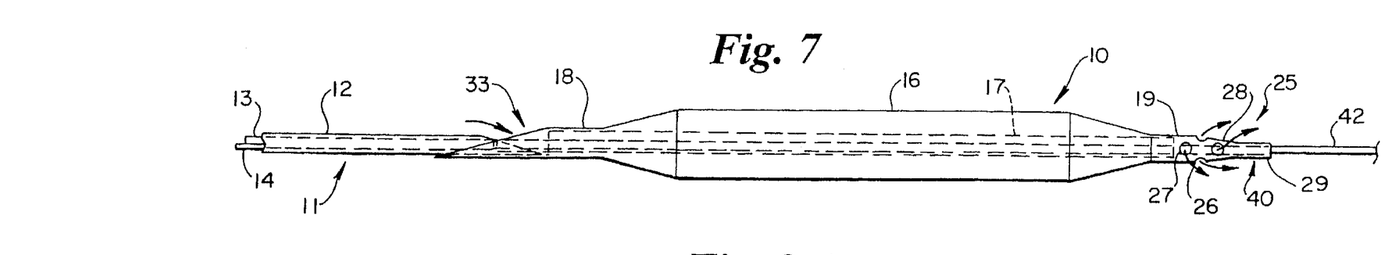
FIG. 7 is a side elevational view of another embodiment of the balloon catheter.

FIGS. 7–17 and 27 illustrate an additional embodiment encompassed by the present invention. In many respects, the additional embodiment is similar to, or the same as, the embodiment described with reference to FIGS. 1–6, including the use of an integrally formed, i.e. made from one piece as shown in FIGS. 1 and 7, balloon/projecting tip assembly. Consequently, only differences between the embodiments will be described with reference to FIGS. 7–14.

Figure 8:
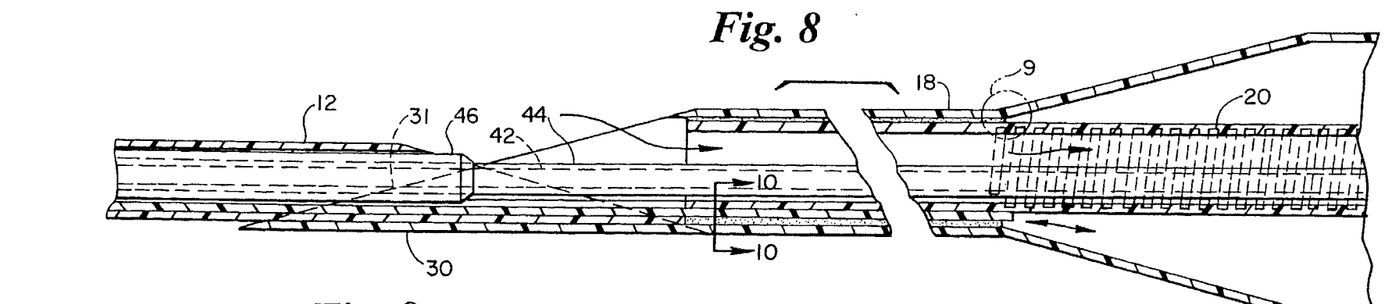
FIG. 8 is a greatly enlarged fragmentary detail thereof sectioned vertically along the longitudinal axis and having some parts unsectioned for clarity.
Figure 9:
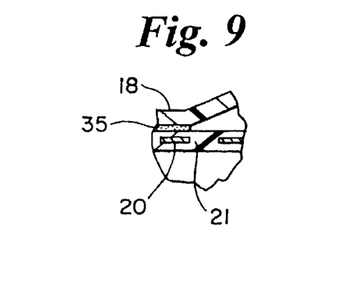
FIG. 9 is a fragmentary detail thereof and enlarged therefrom in the area encircled at 9 in FIG. 8.
Figure 10:
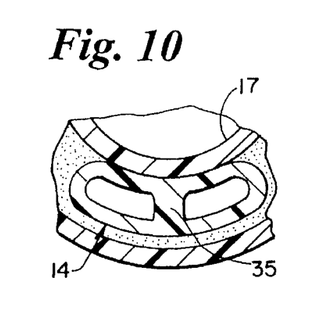
FIG. 10 is a greatly enlarged fragmentary detail view thereof taken generally along line 10—10 in FIG. 8.
Figure 11:
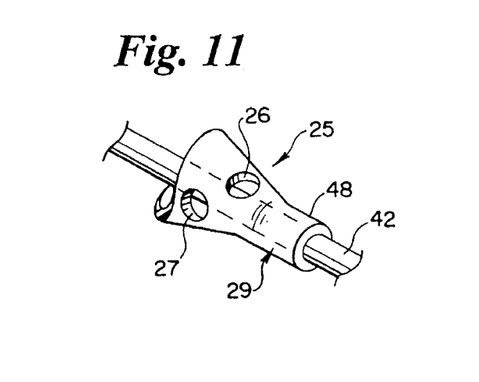
Figures 12, 15:
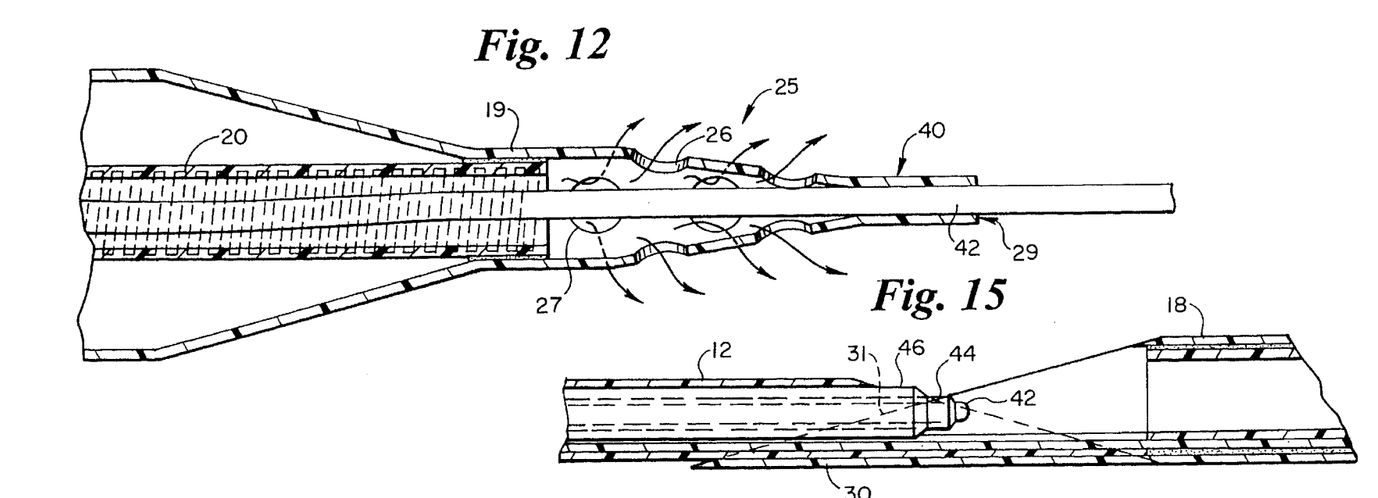
FIG. 12 is a fragmentary detail thereof sectioned vertically along the longitudinal axis and showing the guide wire protruding through distal end thereof.
FIG. 15 is a greatly enlarged fragmentary detail thereof sectioned vertically along the longitudinal axis showing the guide wire and axially displaceable guide wire tube withdrawn.
Figure 13:
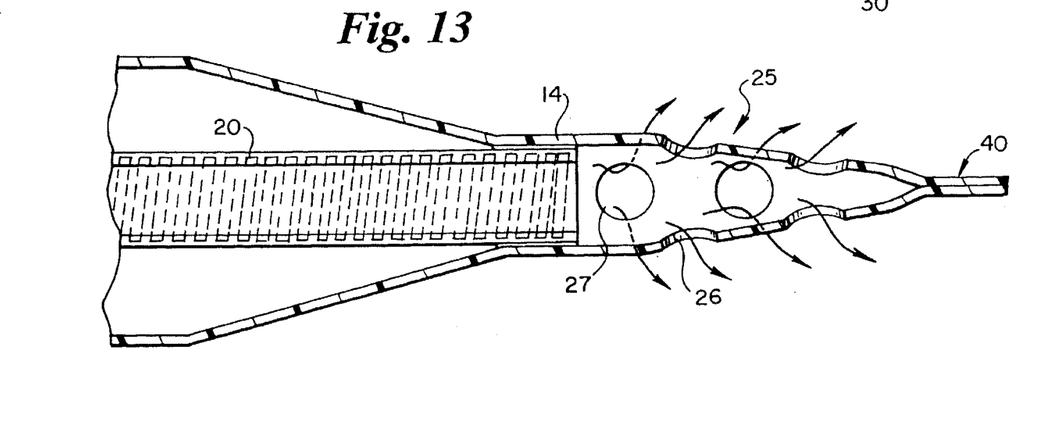
FIG. 13 is a view similar to that of FIG. 12 showing guide wire withdrawn.

In the first embodiment described herein, the guide wire extends through an axially fixed guide wire tube 46, through the balloon envelope 16, and into and including the discharge lumen 40. The guide wire 42 of this embodiment extends through an axially positionable guide wire tube 44 which, in turn, extends through the fixed guide wire tube 46, and through the balloon envelope 16 and into the discharge lumen 40. Fixed tube 46 has a distal end which terminates just prior to the proximal perfusion opening. FIG. 11 illustrates guide wire 42 as extending through discharge lumen 40 forming the distal end of balloon assembly tip 25. As best illustrated in FIG. 8, the fixed guide wire tube 46 is mounted concentrically about the axially displaceable guide wire displaceable tube 44, and relative telescoping movement of the displaceable tube 44 with respect to the fixed tube 46 is permitted. The fixed tube 46, as can be seen, obviously has a diameter which is larger than that of the displaceable tube 44, and displaceable tube 44 has a diameter which is larger than that of guide wire 42.

As previously discussed in this document, under certain circumstances it is advantageous not only to minimize the length of time during which blood flow during dilatation might be occluded, but also to maximize perfusion when perfusion is afforded. To facilitate maximization of perfusion, once the catheter has been installed at a desired location, displaceable tube 44 could be withdrawn from the perfusion lumen 17 and into the fixed tube 46. Because the guide wire 42 is unconstrained by displaceable tube 44, the cross-sectional area of the perfusion lumen 17 will be significantly increased in view of the absence of displaceable tube 44. Perfusion will be increased commensurately.

Figure 14:
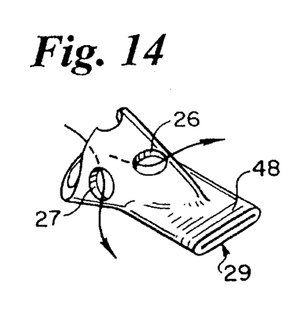
FIG. 14 is a view similar to that of FIG. 11 having guide wire withdrawn.

In some cases, it might be desirable to occlude or at least minimize egress of perfused blood through the main axial orifice at the distal end of the discharge lumen 40 defining the balloon assembly tip 25. In the embodiment of FIGS. 7–17 and 27, the guide wire 42 is shown as passing through the balloon assembly tip discharge lumen 40. With the guide wire 42 in this position, perfusion will pass primarily through the side wall orifices 26, 27. If the guide wire 42 is withdrawn, however, a gate (as seen at 48) defined by the distal end of the discharge lumen 40 can be made to close automatically. This can be accomplished by making the distal end of the discharge lumen 40 from a resilient material and pre-biasing it to a closed position as best seen in FIG. 14. Initial passage of the guide wire 42 through the discharge lumen 40 will effect overcoming of this bias to enable passage of the guide wire 42 through the discharge lumen 40. Once the guide wire 42 is withdrawn, however, the gate 48 will return to its normally closed disposition so that perfused fluid will pass through the side wall orifices 26, 27. As discussed hereinbefore, FIG. 14 illustrates gate 48 as being in a closed disposition. In this disposition, gate 48 will substantially preclude flow of perfused blood through the main axial orifice at the distal end of the discharge lumen 40. It will be understood, however, that, for example, the structure illustrated in FIG. 11, wherein guide wire 42 passes through gate 48, flow of perfused blood through the main axial orifice at the distal end of the discharge lumen 40 will also be precluded. With guide wire 42 left in place, therefore, as illustrated in FIG. 11, perfusion will pass primarily through the side wall orifices 26, 27 also.

Figure 16:
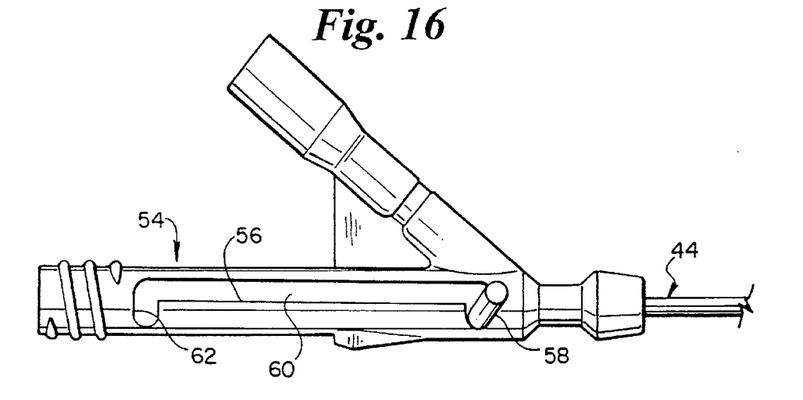
FIG. 16 is a fragmentary side elevational view of a manipulator at the proximal end of the catheter wherein the axially displaceable guide wire tube is extended.
Figure 17:
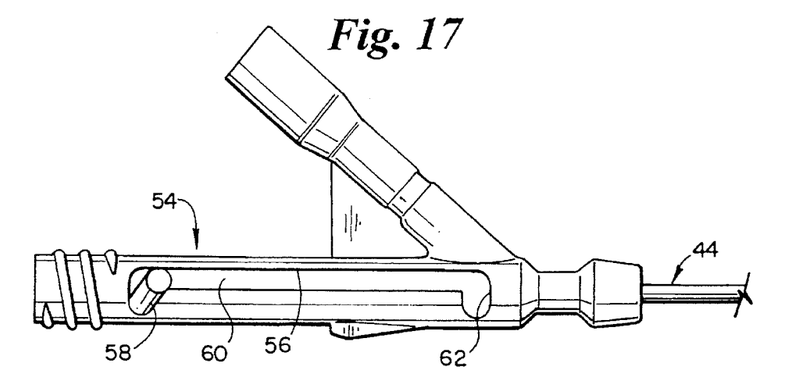
FIG. 17 is a fragmentary side elevational view of a manipulator at the proximal end of the catheter wherein the axially displaceable guide wire tube is withdrawn.

FIGS. 16–17 illustrate structure, disposed external to the patient upon which angioplasty were being performed, for controlling the axial positioning of the displaceable guide wire tube 44. These two figures show a handle 54 having an axial slot 56 formed therein. A pin 58 extends radially outwardly from a sleeve 60, received within the handle 54 and attached, either directly or indirectly, to the displaceable guide wire tube 44. The pin 58 is movable along the slot 56 to effect extension or withdrawal of the displaceable guide wire tube 44 to accomplish axial movement thereof. As seen in FIGS. 16 and 17, both ends of the slot are provided with 90° turns 62 within which the pin 58 can be captured in order to maintain displaceable guide wire tube 44 at a desired defined axial location. In the case of the pin position illustrated in FIG. 16, the displaceable guide wire tube 44 would be extended. With the pin 58 in the location as illustrated in FIG. 17, the tube 44 would be retracted into fixed guide wire tube 46.

Figures 23, 24, 25, 26, 27:
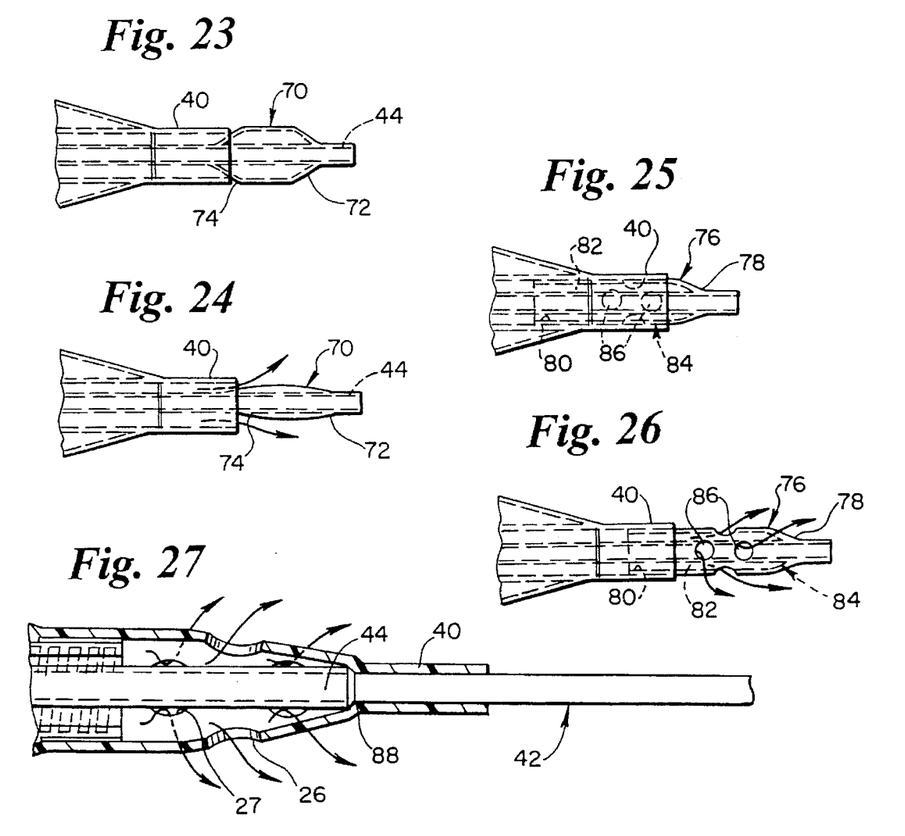
FIG. 23 is similar to FIGS. 18 and 20 showing a further valving embodiment.
FIG. 24 is a view similar to FIGS. 19 and 22 showing the valving embodiment of FIG. 23 in an open disposition.
FIG. 25 is a view similar to FIGS. 18, 20, and 23 showing an additional valving embodiment.
FIG. 26 is a view similar to FIGS. 19, 22, and 24 showing the valving embodiment of FIG. 25 in an open disposition.
FIG. 27 is a view similar to FIGS. 12 and 13 illustrating an additional valving method.

FIG. 27 illustrates, with more specificity, a preferred structure of the axially displaceable guide wire tube 44. As can be seen in this figure, the displaceable guide wire tube 44 can be axially extended so that a distal, beveled end 88 of the tube 44 can engage the proximal end of the discharge lumen 40 to alter perfusion flow outwardly through lumen 40 and allow wire backloading by sealing the interface between beveled end 88 and the proximal end of discharge lumen 40.

It will be understood that, when the guide wire 42 is constrained by a displaceable guide wire tube 44 along its run through perfusion lumen 17, perfusion still could be increased when the guide wire 42 is withdrawn. This would be accomplished by making the displaceable guide wire tube 44 collapsible so that the cross-sectional area of the collapsed guide wire tube 44 would be significantly smaller than the cross-sectional area of the displaceable guide wire tube 44 when it constrains the guide wire 42. In the case of a collapsible displaceable guide wire tube 44, while perfusion will not be increased to the degree that it would when the displaceable guide wire tube 44 is retracted, perfusion would be significantly increased.

Figure 18:
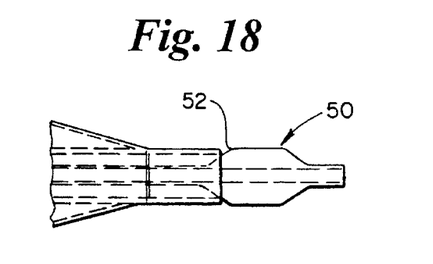
FIG. 18 is a fragmentary side elevational view of an alternate embodiment having the axially displaceable guide wire tube retracted to valve the distal end of catheter closed.
Figure 19:
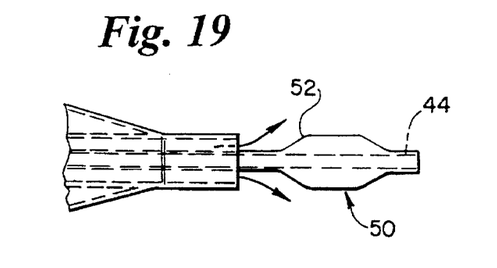
FIG. 19 is a fragmentary side elevational view of an alternate embodiment having the axially displaceable guide wire tube advanced to valve the distal end of catheter open.

FIGS. 18–19 illustrate another embodiment for controlling, metering, and occluding flow through the main axial orifice at the distal end of the discharge lumen 40. These two figures show a radially expanded portion 50 of the displaceable guide wire tube 44 which is located proximate the distal end of the discharge lumen 40. It will be understood that, with this embodiment, the gate biased to a closed position, as described hereinbefore, would not be employed. Rather, the discharge lumen would be maintained with a constant cross-section. In this embodiment, it will be understood, the radially expanded portion 50 of the displaceable guide wire tube 44 would be larger than the main axial orifice in the discharge lumen 40. Consequently, when the displaceable guide wire tube 44 is retracted to a position as illustrated in FIG. 18, a shoulder 52 defined by the expanded portion of the displaceable guide wire tube 44 would engage the distal end of the discharge lumen 40 to occlude egress flow of perfused fluid through the main axial orifice. When such flow is precluded, the perfused blood will pass through the side wall orifices 26, 27 and reduce trauma during catheter withdrawal or advancement.

On the other hand, when the displaceable guide wire tube 44 is extended so that the expanded portion 50 thereof is spaced from the distal end of the discharge lumen 40, as seen in FIG. 19, egress flow through the main axial orifice will be permitted. It will be understood that, the greater the distance the expanded portion 50 of the displaceable guide wire tube 44 is spaced from the distal end of the discharge lumen 40, the greater the flow of blood through the main axial orifice will be. The closer the expanded portion 50 of the displaceable guide wire tube 44 is brought to the discharge lumen distal end, the more egress flow through that orifice will be restricted. The mechanism illustrated in, and described with reference to, FIGS. 16 and 17 can also be employed for controlling the positing of the displaceable guide wire tube 44 relative to the discharge lumen 40.

Figure 20:
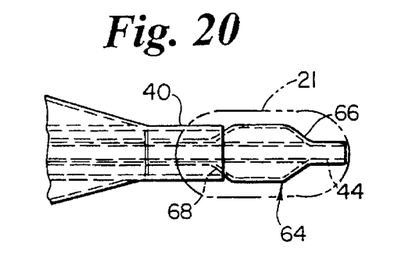
FIG. 20 is a view similar to FIG. 18 illustrating another valving embodiment.
Figure 21:
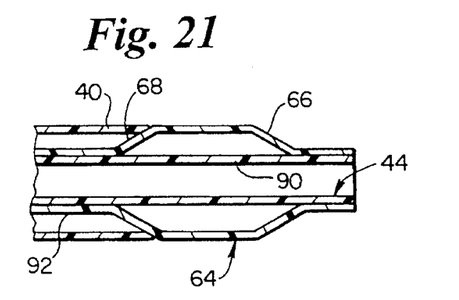
FIG. 21 is a greatly enlarged fragmentary detail view showing the construction of the valving structure.
Figure 22:
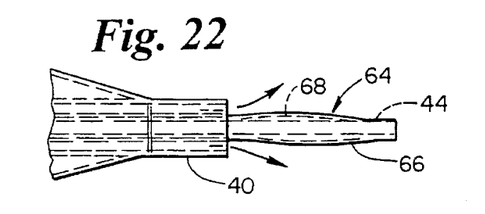
FIG. 22 is a view similar to FIG. 19 showing the additional valving embodiment with the distal end of the catheter open.

FIGS. 20–22 illustrate another structure by which the valving of the distal and of the discharge lumen 40 can be accomplished. In this embodiment, an elastomeric element 64 is mounted at a desired axial location along the displaceable guide wire tube 44. The location is dictated by a disposition at which the elastomeric element 64 will occlude the distal end of the discharge lumen 40.

FIG. 21 illustrates the elastomeric element 64 which can be used in combination with a two-part displaceable guide wire tube 44. The distal end 66 of the elastomeric element is shown as being fixedly attached to an inner tube member 90 of displaceable guide wire tube 44. A proximal end 68 of the elastomeric element 64 is, in turn, fixedly attached to an outer tube member 92 of the displaceable guide wire tube 44. The inner tube member 90 and outer tube member 92 are selectively telescopable relative to one another. As will be able to be seen then, as inner tube member 90 is urged outwardly relative to outer tube member 92, the elastomeric element will be stretched longitudinally and will, concurrently, deform radially inwardly. On the other hand, if members 90, 92 are telescoped in an opposite relative relationship, the elastomeric element 64 will be deformed radially outwardly and achieve a configuration as seen in FIGS. 20 and 21. With the elastomeric element in such a configuration, the displaceable guide wire tube 44 can be withdrawn so that the element 64 engages the distal end of the discharge lumen 40 to occlude egress flow through the main axial orifice. It will be understood that any appropriate structure for effecting radially inward and outward deformation of elastomeric element 64, such as the use of a push wire, connected to either the distal or proximal end of the elastomeric element, is within the scope of the invention.

FIGS. 23 and 24 illustrate another embodiment of a valving mechanism. In this embodiment both distal and proximal ends 72, 74 of the valving element 70 are secured, in any appropriate manner, to the displaceable guide wire tube 44. The valving element 70 of this embodiment can, normally, be in a flaccid state. The element 70 can, however, be inflated, selectively, by actuation of means not shown. When inflated, the element 70 takes a form and size so as to be able to occlude the main axial orifice at the distal end of the discharge lumen 40. It will be understood that, with this embodiment, no relative axial movement of the displaceable guide wire tube 44 need be accomplished, since the radial dimension of the element 70 is not dependent upon axial movement of the displaceable guide wire tube 44.

FIGS. 25 and 26 illustrate another valving embodiment. In this embodiment, a sleeve 76 is mounted at a desired axial location along the displaceable guide wire tube 44. The location and size and dimensions of the sleeve 76 are such that the sleeve, being mounted generally concentrically with regard to the displaceable guide wire tube 44, can, at a determined axial position of the displaceable guide wire tube 44, occlude the discharge lumen 40. The sleeve 76 is provided with a closed distal end 78 by which it is mounted to the displaceable guide wire tube 44. The opposite, proximal end 80 of the sleeve 76 is open so that blood perfused through the perfusion lumen 17 can fill an annular space 82 between the displaceable guide wire tube 44 and the sleeve 76. The sleeve 76 is defined by an outer wall 84 which has a cross section approximating the cross section of the discharge lumen 40. It is for this reason that, with the displaceable guide wire tube 44 at a designated axial location, occlusion of the main axial orifice at the distal end of the discharge lumen 40 can be afforded.

At least one port is formed in the outer wall 84 by which the sleeve 76 is defined. FIG. 25, however, shows a series of ports 86 formed in the wall 84. FIG. 25 shows a series of six ports 86. Two ports are formed in the wall 84 at 180° relative to one another. A second pair of ports are axially spaced and circumferentially displaced at 90° relative to the first pair of ports. A third pair of ports is again axially spaced from the second pair of ports and circumferentially displaced at 90°.

FIG. 25 illustrates all six ports 86 being formed in the wall 84 so that, with the axial positioning of the displaceable guide wire tube 44 shown, all six ports are occluded by the discharge lumen 40. FIG. 26, on the other hand, shows axial movement of the displaceable guide wire tube 44 sufficient to expose all of the ports 86 so that they are not covered by the discharge lumen 40. In this position of the sleeve 76, the ports 86 afford egress of perfused blood through the ports.

Obviously many modifications and variations of the present invention are possible in light of the above teachings. For example, while some material preferences have been indicated, any suitable material may be employed. Also, while a preferred array of discharge orifices is discussed above, other arrays of elongated discharge orifices may be employed to facilitate perfusion discharge. Indeed, the several teachings herein may be usefully employed in other perfusion applications. It is therefore to be understood that, within the scope of this appended claims, the invention may be practiced otherwise than as specifically described.

What is claimed is:

1. In a balloon angioplasty catheter of the type having a balloon assembly carried at a distal end of an elongated catheter body and means for inflating a balloon envelope of said assembly, the balloon assembly including said balloon envelope and a perfusion lumen having a distal end extending through the balloon envelope to provide a blood flow passage during inflation of the balloon envelope; the improvement which comprises a projecting balloon assembly tip integrally formed with the balloon envelope and extending beyond the distal end of the perfusion lumen to define a discharge lumen, the integral projecting tip including a side wall, tapering radially inwardly in a distal direction, having at least one generally elliptical perfusion discharge orifice, elongated along an axis generally parallel to a longitudinal axis of the projecting balloon assembly tip, formed therein.

2. The balloon angioplasty catheter of claim 1 further comprising a second lumen for removably inserting a guide wire into the catheter, that extends through the balloon envelope and distally through the projecting integral tip, the projecting integral tip having a plurality of generally elliptical discharge orifices through the side wall.

3. The balloon angioplasty catheter of claim 2 wherein the discharge orifices have their major dimension generally aligned with the direction of projection of the integral tip.

4. The balloon angioplasty catheter of claim 3 wherein the aspect ratio of the generally elliptical discharge orifices is 1.5 to 1.0.

5. The balloon angioplasty catheter of claim 2 wherein the projecting integral tip has a region of discharge-facilitating distally decreasing cross-section.

6. The balloon angioplasty catheter of claim 5 wherein the discharge orifices are generally elliptical having their major dimension generally aligned with the direction of projection of the integral tip and are located in the region of distally decreasing cross-section.

7. The balloon angioplasty catheter of claim 6 wherein the aspect ratio of the generally elliptical orifices is 1.5 to 1.0.

8. The balloon angioplasty catheter of claim 1 wherein the perfusion lumen is formed of an encapsulating flexible material supported against collapse during balloon envelope inflation by a support member having spaced elements.

9. The balloon angioplasty catheter of claim 8 wherein the support member is a helical member formed of wound ribbon.

10. The balloon angioplasty catheter of claim 9 wherein the flexible material encapsulates the helical member along its length.

11. The balloon angioplasty catheter of claim 9 wherein the helical member includes spaced coils having a pitch that is selected to avoid coil-to-coil contact during traverse of a body vessel.

12. The balloon angioplasty catheter of claim 9 wherein the helical member is a surgical grade stainless steel.

13. The balloon angioplasty catheter of claim 9 wherein the helical member is radiopaque.

14. The balloon angioplasty catheter of claim 1 wherein the balloon assembly includes a proximal tubular waist extension having inner cross-sectional dimensions greater than the outside dimensions of the catheter body distal end, the catheter body distal end being secured within the balloon assembly waist extension to define an axial flow opening to the perfusion lumen.

15. The balloon angioplasty catheter of claim 14 wherein the balloon assembly waist is skived to elongate the flow opening in the direction of flow.

16. The balloon angioplasty catheter of claim 14 wherein the balloon assembly waist and catheter body distal end are skived to elongate the flow opening in the direction of flow.

17. In a balloon angioplasty catheter of the type having a balloon, means for inflating the balloon, and a perfusion lumen extending through the balloon to provide a blood flow passage during balloon inflation and a blood discharge lumen extending distally of the balloon, the discharge lumen including at least one side discharge orifice; the improvement wherein said discharge lumen is defined by a side wall, tapering radially inwardly in a distal direction, and wherein said at least one side discharge orifice is elongated along an axis, generally parallel to a longitudinal axis of extension of the discharge lumen, and is formed in said side wall.

18. The balloon angioplasty catheter of claim 17 wherein the elongated discharge orifice is generally elliptical.

19. The balloon angioplasty catheter of claim 18 wherein the aspect ratio of the generally elliptical orifices is 1.5 to 1.0.

20. The balloon angioplasty catheter of claim 17 wherein the discharge lumen has a region of discharge-flow-facilitating, distally-decreasing cross-section.

21. The balloon angioplasty catheter of claim 20 wherein the elongated discharge orifice is generally elliptical.

22. The balloon angioplasty catheter of claim 21 wherein the aspect ratio of the generally elliptical orifices is 1.5 to 1.0.

23. In a balloon angioplasty catheter of the type having a balloon assembly carried at a distal end of an elongated catheter body and means for inflating a balloon envelope of said assembly, the balloon assembly including said balloon envelope and a perfusion lumen extending through the balloon envelope to provide a blood flow passage during inflation of the balloon envelope, and the catheter having a guide wire extending, during catheter installation, from the catheter body to a discharge lumen through the perfusion lumen; the improvement which comprises a projecting balloon assembly tip integrally formed with the balloon envelope and extending beyond the distal end of the perfusion lumen to define the discharge lumen in fluid communication with the perfusion lumen, the integral projecting tip including at least one perfusion discharge orifice formed therethrough, and a tip distal end defining a gate through which the guide wire, during catheter installation, passes, the gate being biased to a closed position so that, when the guide wire is withdrawn from a disposition passing through the perfusion lumen, the gate closes, and further including an axially-displaceable, collapsible guide wire tube, through which the guide wire, during installation, extends, extending distally from the catheter body, through the perfusion lumen, and into the projecting integral tip, the projecting integral tip having a plurality of side discharge perfusion orifices, the axially-displaceable guide wire tube collapsing upon withdrawal of the guide wire.

24. The balloon angioplasty catheter of claim 23 wherein the side discharge perfusion orifices are generally oval having their major dimension generally aligned with the direction of projection of the integral tip.

25. In a balloon angioplasty catheter of the type having a balloon assembly carried at a distal end of an elongated catheter body and means for inflating a balloon envelope of said assembly, the balloon assembly including said balloon envelope and a perfusion lumen extending through the balloon envelope to provide a blood flow passage during inflation of the balloon envelope, and the catheter having a guide wire extending through an axially-displaceable guide wire tube, during catheter installation, from the catheter body to a discharge lumen through the perfusion lumen; the improvement which comprises means for metering perfusion through the perfusion lumen and discharge lumen including a valve member carried by the displaceable guide wire tube and selectively movable, relative to a distal end of the discharge lumen by axial movement of the displaceable guide wire tube, between a first position, wherein perfusion through the perfusion lumen and the discharge lumen is precluded, and at least one second position, wherein perfusion through the perfusion lumen and the discharge lumen is afforded.

26. The balloon angioplasty catheter of claim 25 wherein the valve member comprises a radially expanded element carried by the displaceable guide wire tube at a location therealong distal with respect to the distal end of the discharge lumen, the radially expanded element carried by the displaceable guide wire tube having a cross-sectional shape and area sufficient to define a shoulder engagable with the distal end of the discharge lumen to restrict and occlude egress flow through the discharge lumen when the displaceable guide wire tube is withdrawn with respect to an extended position thereof.

27. The balloon angioplasty catheter of claim 26 wherein the radially expanded element is selectively expandable and contractable.

28. The balloon angioplasty catheter of claim 27 further comprising means for selectively expanding and contracting the radially expanded element.

29. The balloon angioplasty catheter of claim 28 wherein the means for selectively expanding and contracting the radially expanded element comprises a resilient envelope inflatable by injection of fluid into the envelope.

30. The balloon angioplasty catheter of claim 28 wherein the means for selectively expanding and contracting the radially expanded element comprises an elastomeric envelope normally expanded radially to have a size and shape so as to restrict and occlude egress flow through the discharge lumen, the elastomeric envelope having a proximal axial end positionable axially proximate the distal end of the discharge lumen, and a distal axial end fixed to the displaceable guide wire tube at a location spaced outwardly from the distal end of the discharge lumen, wherein, as the distal axial end of the elastomeric envelope fixed to the displaceable guide wire tube is urged outwardly in a directly of perfusion flow through the perfusion lumen, the elastomeric envelope becomes elongated axially and, commensurately, deformed radially inwardly to afford egress flow through the discharge lumen.

31. The balloon angioplasty catheter of claim 26 wherein the valve member comprises a sleeve mounted to the displaceable guide wire tube generally concentrically enclosing the displaceable guide wire tube, the sleeve having a closed distal end by which it is mounted to the displaceable guide wire tube, an open proximal end, and an outer wall with a cross section approximating a cross section of the discharge lumen, and at least one port formed therethrough, wherein, in one axial position of the displaceable guide wire tube, the at least one port formed in the wall of the sleeve is occluded by the discharge lumen and, in an outward axially displaced position of the displaceable guide wire tube, the at least one port in the wall of the sleeve is unoccluded to afford fluid flow therethrough.

32. In a balloon angioplasty catheter of the type having a balloon assembly carried at a distal end of an elongated catheter body and means for inflating a balloon envelope of said assembly, the balloon assembly including said balloon envelope and a perfusion lumen extending through the balloon envelope to provide a blood flow passage during inflation of the balloon envelope, and the catheter having a guide wire extending from the catheter body to a discharge lumen through the perfusion lumen; the improvement which comprises a guide wire having a cross section smaller than the discharge lumen so as to not fully preclude egress flow through the discharge lumen even when the guide wire is positioned extending through the discharge lumen, and an axially-displaceable guide wire tube encircling the guide wire and having a cross section, relative to a cross section of the discharge lumen, to restrict flow through the discharge lumen, the displaceable guide wire tube being movable axially so that, when a distal end thereof is brought into engagement with a shoulder defined at a proximal end of the discharge lumen, egress flow through the discharge lumen is precluded.

33. In a balloon angioplasty catheter of the type having a balloon assembly carried at a distal end of an elongated catheter body, the catheter body including an inflation lumen, the balloon assembly including an inflatable balloon envelope in fluid communication with said inflation lumen and a perfusion lumen having a distal end extending through the balloon envelope to provide a blood flow passage during inflation of the balloon envelope; the improvement which comprises a projecting balloon assembly tip integrally formed with the balloon envelope and extending beyond the distal end of the perfusion lumen to define a discharge lumen, the integral projecting tip including a side wall having at least one generally elliptical perfusion discharge orifice, wherein the balloon assembly includes a proximal tubular waist extension having inner cross-sectional dimensions greater than the outside dimensions of the catheter body distal end, the catheter body distal end being secured within the balloon assembly waist extension to define an axial flow opening to the perfusion lumen.

* * * * *